US 8,549,722 B2

(12) United States Patent
Tenne

(10) Patent No.: US 8,549,722 B2
(45) Date of Patent: Oct. 8, 2013

(54) METHODS FOR MANUFACTURING IMPLANTABLE STENTS HAVING A PLURALITY OF VARYING PARALLELOGRAMMIC CELLS

(75) Inventor: Dirk Tenne, Miami Beach, FL (US)

(73) Assignee: DePuy Synthes Products, LLC, Raynham, MA (US)

(*) Notice: Subject to any disclaimer, the term of this patent is extended or adjusted under 35 U.S.C. 154(b) by 80 days.

(21) Appl. No.: 13/274,421

(22) Filed: Oct. 17, 2011

(65) Prior Publication Data
US 2012/0055011 A1    Mar. 8, 2012

Related U.S. Application Data

(62) Division of application No. 11/690,600, filed on Mar. 23, 2007, now Pat. No. 8,062,347.

(51) Int. Cl.
*B23P 25/00* (2006.01)

(52) U.S. Cl.
USPC .......................................................... 29/458

(58) Field of Classification Search
USPC ........... 29/592, 458, 428; 623/1.15, 1.2, 1.34, 623/1.1, 1.35, 1.37
See application file for complete search history.

(56) References Cited

U.S. PATENT DOCUMENTS

| | | |
|---|---|---|
| 5,503,636 A | 4/1996 | Schmitt et al. |
| 5,707,387 A | 1/1998 | Wijay |
| 6,059,822 A | 5/2000 | Kanesaka et al. |
| 6,346,133 B1 * | 2/2002 | Narasimhan et al. ........... 75/252 |
| 6,436,133 B1 | 8/2002 | Furst et al. |
| 6,530,951 B1 | 3/2003 | Bates et al. |
| 6,612,012 B2 | 9/2003 | Mitelberg et al. |
| 6,673,106 B2 | 1/2004 | Mitelberg et al. |
| 6,818,013 B2 | 11/2004 | Mitelberg et al. |
| 6,833,003 B2 | 12/2004 | Jones et al. |
| 6,932,837 B2 | 8/2005 | Amplatz et al. |
| 6,955,685 B2 | 10/2005 | Escamilla et al. |
| 6,960,227 B2 | 11/2005 | Jones et al. |
| 7,001,422 B2 | 2/2006 | Escamilla et al. |
| 7,025,733 B2 | 4/2006 | McQuaid |
| 7,037,331 B2 | 5/2006 | Mitelberg et al. |
| 7,060,091 B2 | 6/2006 | Killion et al. |
| 8,118,859 B2 * | 2/2012 | Tenne .......................... 623/1.23 |
| 2004/0102834 A1 | 5/2004 | Nakano et al. |
| 2005/0234536 A1 | 10/2005 | Mitelberg et al. |

* cited by examiner

*Primary Examiner* — John C Hong
(74) *Attorney, Agent, or Firm* — Cook Alex Ltd.

(57) ABSTRACT

A stent for implantation within a body vessel is provided with a plurality of varying parallelogrammic cells. The stent is radially expandable from a compressed condition, suitable for inserting the device in an introducer, to a deployed or expanded condition within a body vessel. The stent includes a plurality of parallelogrammic body cells and a plurality of parallelogrammic flare cells. The flare cells have a substantially greater elongation ratio than the body cells. Also provided is a method for manufacturing stents having a plurality of varying parallelogrammic cells.

23 Claims, 3 Drawing Sheets

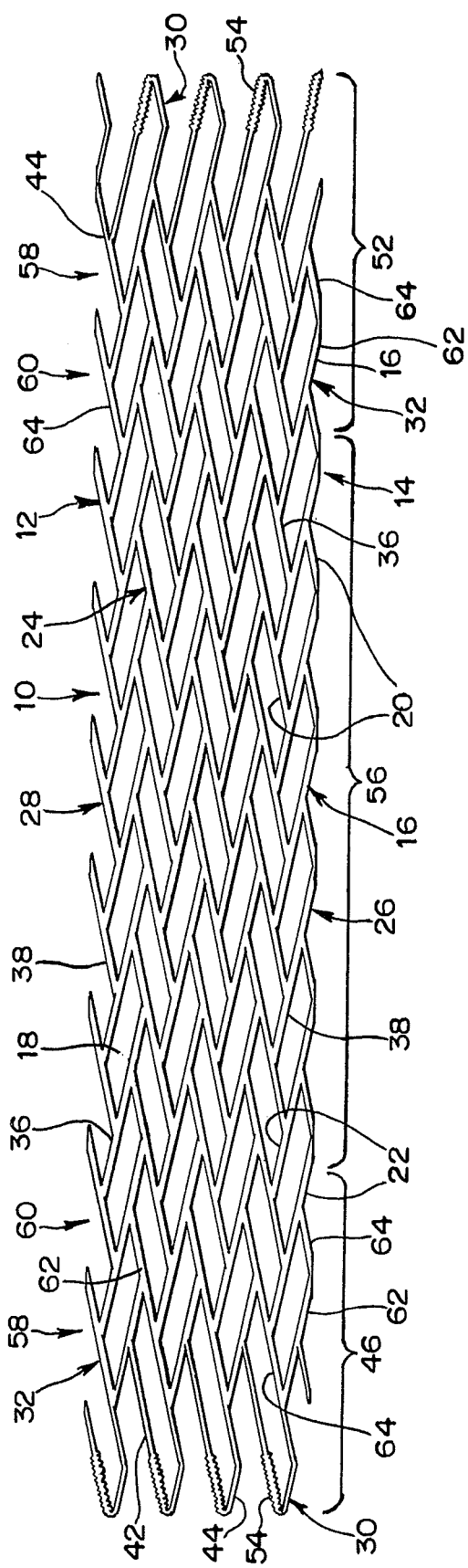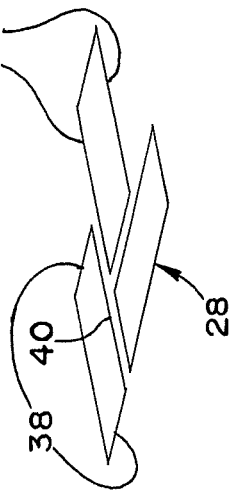

METHODS FOR MANUFACTURING IMPLANTABLE STENTS HAVING A PLURALITY OF VARYING PARALLELOGRAMMIC CELLS

This is a divisional of U.S. patent application Ser. No. 11/690,600, filed Mar. 23, 2007, hereby incorporated by reference hereinto.

DESCRIPTION

1. Field of the Invention

This invention relates to intravascular devices for implantation within a vessel of the body, and more particularly to a stent device which may be used in the treatment of blood vessel disorders. More particularly, this invention relates to stent devices having a plurality of varying parallelogrammic cells and methods for making the same.

2. Description of Related Art

Medical devices that can benefit from the present invention include those that are characterized by hollow interiors and that are introduced endoluminally and expand when deployed. These are devices that move or are moved between collapsed and expanded conditions or configurations for ease of deployment through catheters and introducers. Such devices are typically introduced to a diseased location within a body vessel (e.g., a stenosed section or an aneurysm) and may perform a variety of functions, including support and/or occlusion.

Endoluminal stents typically have a relatively open structure, with a plurality of interconnecting struts which define pores or openings in and/or through the surface that can allow for endothelialization and more permanent fixture of the stent within the vessel after implantation. Certain stents have an especially open structure in order to allow blood flow through the openings and to peripheral arteries after implantation of the stent adjacent to an aneurysm. Typically, the pores or openings are added by masking and/or etching techniques or laser- or water-jet cutting. Known stents include the Cordis Enterprise™ line of self-expanding stents, which are described in numerous patents and published patent applications, including U.S. Pat. Nos. 6,612,012; 6,673,106; 6,818,013; 6,833,003; 6,955,685; 6,960,227; 7,001,422; and 7,037,331 and U.S. Patent Application Publication No. 2005/0234536, all of which are hereby incorporated by reference hereinto.

One potential drawback of known stents is that they may incorporate relatively complicated strut or cell structures that may prohibit easy manipulation of the design, such as when the diameter of the stent is changed. For example, from a manufacturing perspective, a stent design may have cell shapes and characteristics that are well suited to achieve desired effects or operational characteristics when manufactured at a given nominal size or diameter, but these shapes or characteristics may have to be changed or adjusted to maintain identical operational characteristics for a stent manufactured with a different nominal size or diameter. Further, when the struts and/or cells are formed using a laser- or water-cutting process, a complicated pattern may require a high degree of cutting time.

Accordingly, there is a need for an approach to provide stents having an improved cell structure, particularly one that incorporates relatively uncomplicated cell structures and that accommodates manufacture of stents of differing nominal sizes without having to redesign cells during manufacturing. A need remains for a stent cell scheme that facilitates achieving desired hemodynamics in the body vessel and the chronic outward force and radial resistive force of the stent needed for a variety of nominal sizes through variations with cells of identical shapes.

SUMMARY

In accordance with an aspect of the present invention, a stent is provided with a cell structure having a plurality of substantially parallelogrammic body cells, each body cell being defined by a pair of parallel long body cell struts intersecting a pair of parallel short body cell struts. The cell structure further includes a plurality of substantially parallelogrammic flare cells, each flare cell being defined by a pair of parallel long flare cell struts intersecting a pair of parallel short flare cell struts. An elongation ratio of each flare cell is substantially greater than an elongation ratio of each body cell. The stent also includes a plurality of connecting cells, each connecting cell being defined by two pairs of parallel and intersecting connecting cell struts, with selected connecting cells being adjacent to at least one body cell and at least one flare cell.

In accordance with another aspect of the present invention, a stent is provided with a cell structure having a body portion including a plurality of substantially parallelogrammic body cells. Each body cell is defined by a pair of parallel long body cell struts intersecting a pair of parallel short body cell struts. The stent also has end portions at opposite ends of the body portion, and at least one of the end portions includes a plurality of substantially parallelogrammic flare cells. Each flare cell is defined by a pair of parallel long flare cell struts intersecting a pair of parallel short flare cell struts. An elongation ratio of each flare cell is substantially greater than an elongation ratio of each body cell.

In accordance with yet another aspect of the present invention, a method of manufacturing a stent includes providing a tubular member in a compressed condition. A plurality of substantially parallelogrammic body cells and flare cells then are formed in the tubular member. Each body cell is defined by a pair of parallel long body cell struts intersecting a pair of parallel short body cell struts, while each flare cell is defined by a pair of parallel long flare cell struts intersecting a pair of parallel short flare cell struts. An elongation ratio of each flare cell is substantially greater than an elongation ratio of each body cell.

A general object of the present disclosure is to provide endoprostheses or stents that can be manufactured with different nominal sizes or diameters through variations in a set of cells that do not vary in shape from one nominal diameter to another.

Other aspects, objects and advantages of the present invention, including the various features used in various combinations, will be understood from the following description according to preferred embodiments of the present invention, taken in conjunction with the drawings in which certain specific features are shown.

BRIEF DESCRIPTION OF THE DRAWINGS

FIG. 1 shows a cell pattern for a stent according to an aspect of the present invention;

FIG. 2 is a detail view of body cells illustrated in FIG. 1;

FIG. 3 is a detail view of flare cells and a connecting cell illustrated in FIG. 1;

DESCRIPTION OF ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 4:
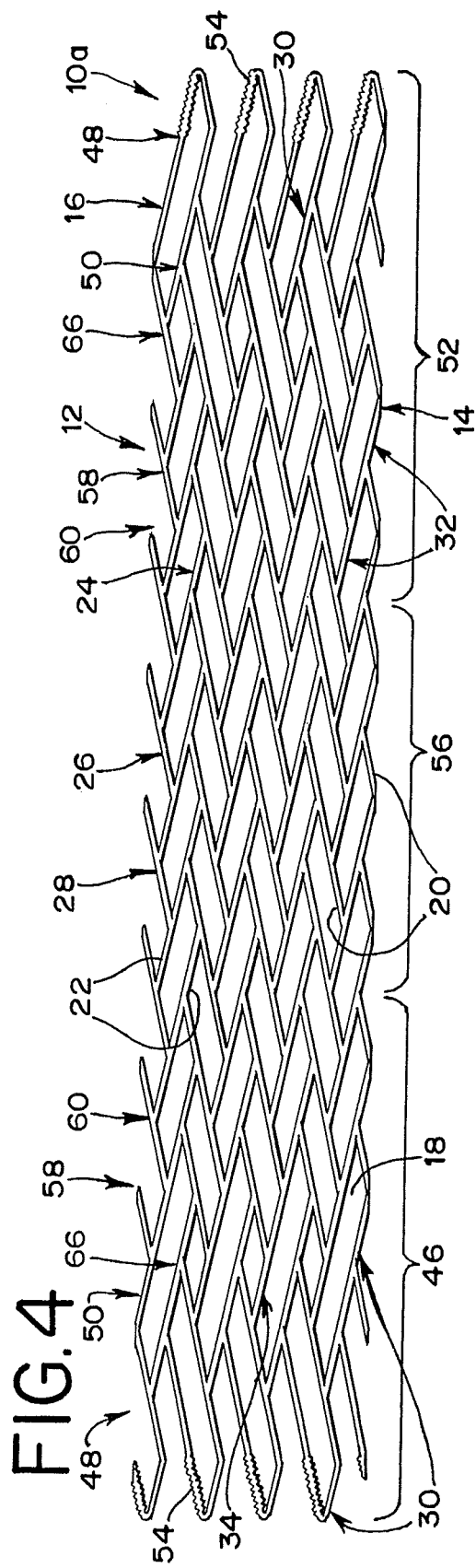
FIG. 4 shows another embodiment of a cell pattern for a stent according to an aspect of the present invention.

FIGS. 1 and 4 show cell patterns 10 and 10a suitable for use with stents implantable within a body vessel. A stent incorporating a cell pattern according to the present invention can be understood by visualizing the pattern 10, 10a being formed into a tube by connecting the top edge 12 with the bottom edge 14. A pattern according to FIG. 1 or 4, for example, is typically sufficient for an entire stent, but the pattern may also be repeated along the surface of the stent without departing from the scope of the present invention. Cell patterns according to the present invention may be used in connection with self-expanding or balloon-expandable stents, but they typically are more advantageous when used in connection with self-expanding stents.

The cell patterns 10 and 10a include a plurality of parallelogrammic cells 16. The patterns of FIGS. 1 and 4 are shown in an "as formed" condition, but it will be understood that a stent incorporating a pattern according to the present invention may be expandable to a larger diameter in a body vessel, in which condition the cells will deform from the illustrated configuration.

Each parallelogrammic cell 16 of FIGS. 1 and 4 comprises a parallelogrammic opening 18 defined by a pair of parallel short struts 20 intersecting a pair of parallel long struts 22, which are longer than the short struts 20. Typically, each strut is substantially linear, which simplifies the manufacturing process compared to many known curved or otherwise complex strut configurations. Although illustrated in FIGS. 1-5 with sharp vertices, each cell opening 18 may instead be provided with flattened or blunted corners. At smaller opening sizes, it can become difficult to accurately manufacture tight, angular corners and, even if possible, it may be preferred to flatten or round the corners in order to provide more material between adjacent openings, and thereby discourage strut rupture. Hence, when used herein to describe the shape of the openings as-manufactured or in a compressed condition, the term "parallelogram" includes parallelograms with one or more flattened or blunted or rounded corners and/or parallelograms with edges having some nominal degree of curvature.

Preferably, the short struts 20 and the long struts 22 are all inclined with respect to the longitudinal length of the pattern/stent, such that the lowermost point of each opening 18 (with reference to FIGS. 1 and 4) is a corner or vertex, rather than a flat edge. Some of the cells, such as cell 24, have an "upward attitude," meaning that their constituent long struts 22 are upwardly inclined when viewed from left to right such as in FIGS. 1 and 4. Other cells, such as cell 26, have a "downward attitude," meaning that their constituent long struts 22 are downwardly inclined when viewed from left to right as illustrated. It will be appreciated that the patterns of FIGS. 1 and 4 are two-dimensional representations of a portion of a cylindrical surface along a longitudinal axis; therefore, "upward attitude," "upwardly inclined," "downward attitude," and "downwardly inclined" designate a general relationship with respect to the longitudinal axis that has a three-dimensional element that is not explicitly illustrated in FIGS. 1 and 4.

In the illustrated embodiment, each cell having an upward attitude is adjacent to at least one cell having a downward attitude and vice versa. This may be preferred to ensure more predictable and/or desirable behavior when the stent is deployed in a body vessel and the cells deform, typically by an opening action.

More particularly, the cell pattern 10 of the embodiment of FIG. 1 includes parallelogrammic body cells 28, flare cells 30, and connecting cells 32. The cell pattern 10a of the embodiment illustrated in FIG. 4 includes the same, but also includes diamond-shaped connecting cells 34, as described in greater detail herein.

Each body cell 28 (shown in greater detail in FIGS. 2 and 5) is comprised of a pair of parallel long body cell struts 36 intersecting a pair of parallel short body cell struts 38. Preferably, all of the body cells 28 are congruent with each other, with the only variation (if any) being the attitude of the cell.

Figure 5:
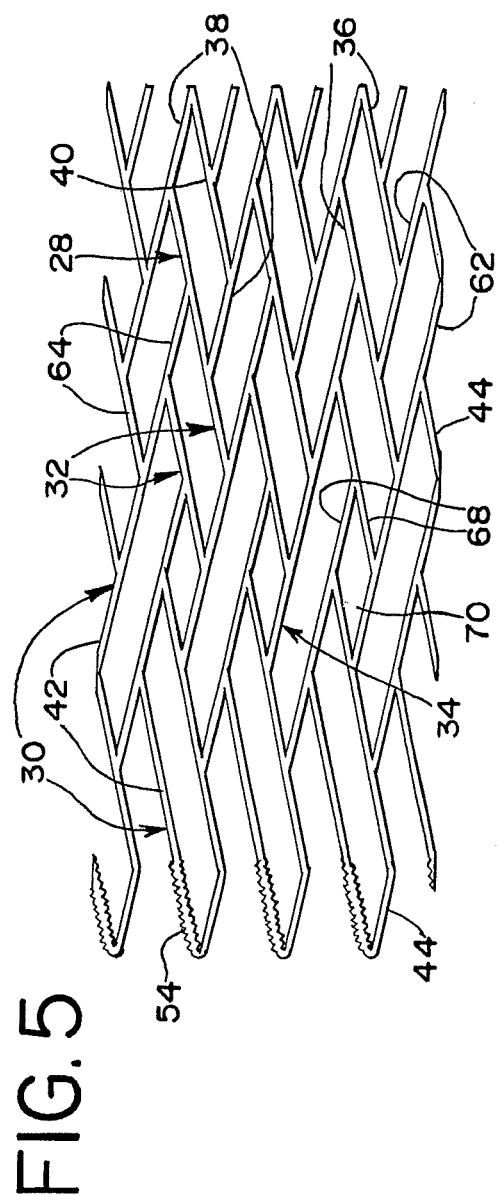
FIG. 5 is a detail view of a portion of the cell pattern of FIG. 4.

The arrangement of each body cell with respect to the body cells adjacent thereto may vary. For example, FIGS. 1 and 2 show a configuration wherein no long body cell strut 36 is intersected at its midpoint, generally designated at 40 in FIG. 2, by another strut. In contrast, FIGS. 4 and 5 illustrate a cell pattern 10a having a configuration in which each long body cell strut 39 is intersected at its midpoint 40 by another strut (FIG. 5). Other configurations may also be used, for example, by incorporating selected long body cell struts which are intersected at their midpoint by another strut and other selected long body cell struts which are not intersected at their midpoint by another strut.

Each flare cell 30 (shown in greater detail in FIGS. 3 and 5) is comprised of a pair of parallel long flare cell struts 42 intersecting a pair of parallel short flare cell struts 44. Preferably, all of the flare cells 30 are congruent with each other, with the only variation (if any) being the attitude of the cell. In the illustrated embodiment, each short flare cell strut 44 has a length less than that of each long flare cell strut 42.

FIG. 1 shows an embodiment of a cell pattern 10 having only a single column of flare cells 30 at each longitudinal end of the pattern. In other configurations, such as the cell pattern 10a of FIG. 4, two or more columns of flare cells adjacent to each other may be included. FIG. 5 shows a proximal end 46 of the pattern 10a of FIG. 4 in greater detail, with an outer column of flare cells, generally designated at 48, and an inner column of flare cells, generally designated at 50. It will be seen in FIG. 4 that a distal end 52 of the pattern 10a is illustrated as having a mirror image of the flare cell configuration of FIG. 5. It may be preferred to have symmetry of this nature to ensure similar operation of the proximal and distal ends of the stent in use, but the configuration of the proximal and distal ends may vary (for example, with the proximal end having multiple columns of flare cells and the distal end having a single column of flare cells, or vice versa) to impart different functionality to each end of the stent.

Figure 6A:
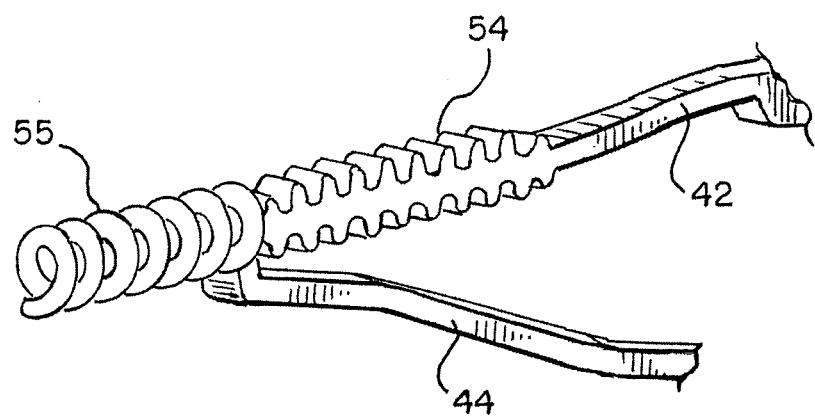
FIGS. 6A and 6B are detail views of a marking system suitable for use with stents according to the present invention.
Figure 6B:
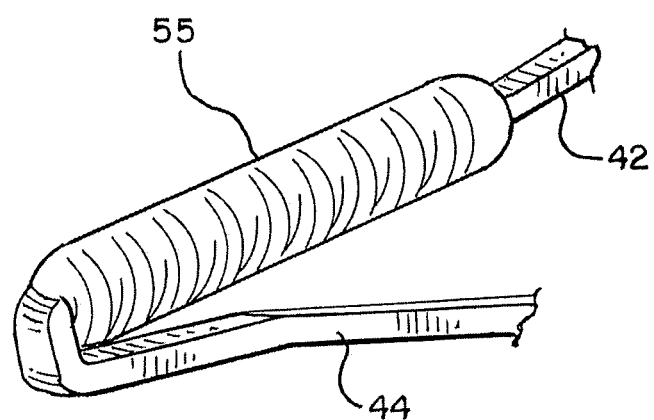

In one embodiment, at least one flare cell 30 is provided with a radiopaque element. In the embodiment of FIGS. 1 and 3, one of the long flare cell struts of each flare cell 30 is provided with a portion, such as of strut 42, having threads 54 formed on same (FIG. 6A), onto which a radiopaque marker band 55 (FIGS. 6A and 6B) may be wound or otherwise applied. Such a method of providing a radiopaque element is described in greater detail in U.S. Pat. No. 6,955,685, which is hereby incorpated by reference hereinto. This aspect of the present invention is not limited to the illustrated example, as the term "radiopaque element" is used broadly and may encompass other methods of providing radiopacity, including but not limited to surface treatment of all or a portion of a flare cell.

In the illustrated embodiments, the cell patterns 10, 10a each are defined by a body portion 56 bounded on opposite sides thereof by a proximal end 46 and a distal end 52. Each end is shown with a plurality of flare cells 30, and it may be preferred for at least one flare cell in each of the proximal and distal ends to have radiopaque properties. FIGS. 1 and 3 show an embodiment in which each flare cell 30 includes a threaded portion 54 for incorporation of a radiopaque element, whereas FIGS. 4 and 5 show an embodiment in which only selected flare cells (illustratively the flare cells in the outer column 48 at each end) include a location such as a threaded portion 54 for a radiopaque element. Other configurations may be used to vary the radiopacity of the stent, and this aspect of the present invention is not limited to the illustrated embodiments. Of course, radiopaque elements may also (or alternatively) be applied to the body cells and/or the connecting cells without departing from the scope of the present invention.

Turning now to the connecting cells 32 and 34, each connecting cell, by definition, is adjacent to at least one flare cell 30 and has a substantially different shape. Each connecting cell may also be adjacent to at least one other connecting cell and/or a body cell 28. In the embodiment of FIGS. 1 and 3, each longitudinal end of the pattern 10 includes an outer column of connecting cells 32, generally designated at 58, adjacent to an inner column of connecting cells 32, generally designated at 60. The columns of connecting cells separate the flare cells 30 from the body cells 28. Each of the illustrated connecting cells 32 is comprised of a pair of parallel long connecting cell struts 62 intersecting a pair of parallel short connecting cell struts 64. As shown, it may be preferred for all of the connecting cells 32 to be congruent with each other, with the only variation (if any) being the attitude of the cell.

FIGS. 4 and 5 illustrate a cell pattern 10a having a different connecting cell configuration. Each end of the pattern 10a includes an outer connecting cell column 58 and an inner connecting cell column 60, with the connecting cells 32 thereof being substantially parallelogrammic, all according to the foregoing description of the connecting cells 32 of FIGS. 1 and 3. However, each end of the cell pattern 10a of FIGS. 4 and 5 also includes a third column of connecting cells, generally designated at 66, wherein each connecting cell 34 of this column is diamond-shaped. As used herein, the term "diamond-shaped" refers to a connecting cell that is comprised of two pairs of parallel struts 68 that intersect each other and have substantially the same length as each other. Although illustrated in FIGS. 4 and 5 with sharp vertices, each diamond-shaped cell opening 70 may instead be provided with flattened or blunted corners. Hence, when used herein to describe the shape of the openings as-manufactured or in a compressed condition, the term "diamond-shaped" includes openings with one or more flattened or blunted or rounded corners and/or openings with edges having some nominal degree of curvature.

Returning now to the body cells 28 and the flare cells 30, the body cells 28 are primarily distinguishable from the flare cells 30 by their shape. In the illustrated embodiments, the short body cell struts 38 are substantially the same length as the short flare cell struts 44, but the long flare cell struts 42 are substantially longer than the long body cell struts 36. The different shapes account for different support characteristics when the stent is deployed to a body vessel and expanded. The body cells 28 allow for a degree of radial expansion, while providing the support strength needed by a target body vessel site. In contrast, the longer flare cells 30 are less rigid, allowing for a greater degree of radial expansion and limiting the force applied to a healthy vessel portion adjacent to the target site. Hence, it may be preferred for the body cells 28 to be positioned in the central body portion 56 of the pattern/stent and the flare cells 30 (along with the connecting cells) to be positioned at opposite ends of the body portion 56, at the proximal end 46 and the distal end 52.

The shape difference between the body cells 28 and the flare cells 30 is generalized by a value referred to herein as the elongation ratio. The elongation ratio of a particular cell may be calculated in a variety of ways, such as by: (1) comparing the length of a constituent long strut to the length of a constituent short strut or (2) comparing the long dimension of the cell opening to the short dimension of the cell opening or (3) taking the average of the ratios calculated by the first two formulations. Those of ordinary skill in the art will appreciate that these calculations will yield slightly different ratios, but the shape difference between the body cells 28 and the flare cells 30 is preferably substantial, such that the differences inherent in the various calculation methods are negligible. For example, in one embodiment the elongation ratio of each flare cell 30 is at least approximately 20% greater than the elongation ratio of each body cell 28. In another embodiment, the elongation ratio of each flare cell 30 is at least approximately 30% greater than the elongation ratio of each body cell 28. In yet another embodiment, the elongation ratio of each flare cell 30 is at least approximately 40% greater than the elongation ratio of each body cell 28. In another example, shown generally in FIGS. 4 and 5, the elongation ratio of each flare cell 30 is approximately 3:1 and the elongation ratio of each body cell 28 is approximately 2:1, meaning that the flare cells 30 are approximately 50% more elongated than the body cells 28 in the "as formed" condition.

The elongation ratios of the body cells 28 and the flare cells 30 and the difference therebetween may be adjusted prior to manufacture to give the resulting stent different performance characteristics. Cells according to the present invention are simple in shape and well-suited for such design changes.

According to one method of manufacturing stents according to the present invention, a substantially cylindrical mandrel (not illustrated) is provided. Typically, the mandrel is sized and configured to approximate the inner diameter of a stent in a deployed or unexpanded condition. Stent material, in one or more layers is added to the exterior surface of the mandrel according to any suitable method to form a tubular member. In one embodiment, the material is a metal having self-expanding properties, such as martensitic nitinol, and may be applied to the mandrel by sputtering. If nitinol is selected as the stent material for a self-expanding stent, it preferably is constituted with a martensite-to-austenite transformation temperature slightly below human body temperature, such that the stent will automatically move to an expanded condition when deployed to a body vessel.

With the stent material positioned on the mandrel, a plurality of parallelogram-shaped openings or cells are formed in the tubular member. These openings have different shapes, corresponding generally to the body cells, flare cells, and parallelogrammic connecting cells of FIGS. 1-5. Other shaped openings, such as the diamond-shaped openings of FIGS. 4 and 5, may be added in addition to the parallelogrammic openings. In one embodiment, the openings are formed by a laser-cutting operation, but other methods, such as etching or water-jet cutting, may also be used without departing from the scope of the present invention. The portions of the tubular member not removed during this step define the struts previously described herein.

With the openings and struts so formed, the processed tubular member, now a stent, is removed from the mandrel. Alternatively, the mandrel can be dissipated at a suitable time in the manufacturing process, precluding the need to otherwise remove same, in which case the mandrel is made of a material that can be dissolved or dissipated without damaging the stent material.

Optionally, one or more thin film meshes or screen members may be applied to the stent before or after it has been removed from the mandrel. Screen members typically are provided with a porosity less than that of the stent when expanded or deployed within a body vessel. Thus, they are useful for applications requiring a lower porosity, with the stent acting as a skeletal support structure for the relatively weak screen member. Any of a variety of screen members may be used in connection with stents of the present invention but, for compatibility purposes, it may be preferred to use a screen member having a pore design similar to the cell pattern of the stent so that the stent and screen member behave similarly when moving to the expanded or deployed condition. Examples of preferred screen members have parallelogrammic pores can be seen in U.S. patent application Ser. No. 11/420,519 and No. 11/420,523 to the present inventor, both of which are hereby incorporated by reference hereinto.

When the stent has been fully removed from the mandrel, it may be used according to any of a number of methods well-known to those of ordinary skill in the art. In one exemplary manner of use, the stent is inserted into the distal end of an introducer (not shown). The stent may be mounted about a guidewire or a balloon catheter before being inserted into the introducer.

When the stent has been properly loaded according to an introducer approach, the introducer is moved into the interior of a body vessel and positioned adjacent to a region of the vessel which is to be occluded. Thereafter, the stent is ejected from the introducer and into the target region. If the stent is not self-expanding, then a balloon is expanded to force the stent against the wall of the vessel.

The stent (and/or screen member if provided) may be coated with an agent, such as heparin or rapamycin, to address stenosis or restenosis of the vessel. Examples of such coatings are disclosed in U.S. Pat. No. 5,288,711 to Mitchell et al.; No. 5,516,781 to Morris et al.; No. 5,563,146 to Morris et al.; and No. 5,646,160 to Morris et al., all of which are hereby incorporated by reference hereinto. Other coatings may also be applied without departing from the scope of the present invention.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A method of manufacturing a stent implantable within a body vessel of a human subject, comprising:

providing a tubular member having a diameter corresponding to a compressed condition, the tubular member having opposite ends, namely a proximal end and a distal end;

forming a plurality of substantially parallelogrammic body cells and flare cells in the tubular member, wherein each body cell is defined by a pair of parallel long body cell struts intersecting a pair of parallel short body cell struts, each flare cell is defined by a pair of parallel long flare cell struts intersecting a pair of parallel short flare cell struts;

said forming includes selecting an elongation ratio of each flare cell, the flare cell elongation ratio being a ratio of long flare cell strut length to short flare cell strut length that is substantially greater than an elongation ratio of each body cell, the body cell elongation ratio being a ratio of long body cell strut length to short body cell strut length; and said forming includes positioning a plurality of the flare cells at said opposite ends.

2. The method of claim 1, further comprising applying a radiopaque element to at least one of said flare cells.

3. The method of claim 1, wherein said forming a plurality of substantially parallelogrammic body cells and flare cells in the tubular member includes providing each flare cell with an elongation ratio at least approximately 20% greater than the elongation ratio of each body cell.

4. The method of claim 1, wherein said forming a plurality of substantially parallelogrammic body cells and flare cells in the tubular member includes providing each flare cell with an elongation ratio of approximately 3:1 and providing each body cell with an elongation ratio of approximately 2:1.

5. The method of claim 1, wherein said forming a plurality of substantially parallelogrammic body cells and flare cells in the tubular member includes providing each of said short flare cell struts with substantially the same length as each of said short body cell struts.

6. The method of claim 1, wherein said forming a plurality of substantially parallelogrammic body cells and flare cells in the tubular member includes forming all of said short body cell struts, long body cell struts, short flare cell struts, and long flare cell struts at an inclination with respect to a longitudinal length of the stent.

7. The method of claim 6, wherein said forming a plurality of substantially parallelogrammic body cells and flare cells in the tubular member includes forming at least one of the body cells with an upward attitude, forming at least one of the body cells with a downward attitude, forming at least one of the flare cells with an upward attitude, and forming at least one of the flare cells with a downward attitude.

8. The method of claim 7, wherein said forming a plurality of substantially parallelogrammic body cells and flare cells in the tubular member includes forming each body cell and each flare cell adjacent to a body cell or flare cell having an opposite attitude.

9. The method of claim 1, wherein said providing a tubular member in a compressed condition includes forming the tubular member from a metallic material having self-expanding properties.

10. A method of manufacturing a stent implantable within a body vessel of a human subject and having a cell structure forming an endoprosthesis, the method comprising:

providing a tubular member having a diameter corresponding to a compressed condition;

forming a plurality of substantially parallelogrammic body cells, wherein each body cell is defined by a pair of parallel long body cell struts intersecting a pair of parallel short body cell struts, the body cells having a body cell elongation ratio of long body cell strut length to short body cell strut length;

forming a plurality of substantially parallelogrammic flare cells, wherein each flare cell is defined by a pair of parallel long flare cell struts intersecting a pair of parallel short flare cell struts, the flare cells having an elongation ratio of long flare cell strut length to short flare cell strut length, and wherein the flare cell elongation ratio is at least approximately 20% greater than the body cell elongation ratio;

forming a plurality of connecting cells, wherein each connecting cell is defined by two pairs of parallel and intersecting connecting cell struts, the struts of the connecting cells have a connecting cell elongation ratio wherein the flare cell elongation ratio is at least approximately 20% greater than the connecting cell elongation ratio, and selected connecting cells are adjacent to at least one body cell and at least one flare cell;

extending each flare cell axially beyond all of the connecting cells such that the entire length of one of the short flare cell struts, the entire length of one of the long flare cell struts (a first flare cell strut) and at least a portion of the length of the other long flare cell struts (a second long flare cell strut) extend axially beyond all of the connecting cells; and spacing apart the flare cells radially with respect to each other to define free space between the first long flare cell strut of one of the flare cells and the second long flare cell strut of the adjacent flare cell.

11. The method of claim 10, further including forming the elongation ratio of each flare cell to be approximately 3:1 and forming the elongation ratio of each body cell to be approximately 2:1.

12. The method of claim 10, further including forming each short flare cell strut to have substantially the same length as each short body cell strut.

13. The method of claim 10, further including inclining all of the connecting cell struts, short body cell struts, long body cell struts, short flare cell struts, and long flare cell struts with respect to a longitudinal length of the stent, wherein at least one of the body cells has an upward attitude, at least one of the body cells has a downward attitude, at least one of the flare cells has an upward attitude, and at least one of the flare cells has a downward attitude.

14. The method of claim 10, further including positioning each body cell and each flare cell adjacent to a body cell or flare cell having an opposite attitude.

15. The method of claim 10, further including forming at least one of the connecting cells to have connecting cell struts having substantially the same length as each other.

16. The method of claim 10, further including forming connecting cells other than the selected connecting cells to have connecting cell struts having substantially the same length as each other.

17. A method of manufacturing a stent implantable within a body vessel of a human subject and having a cell structure forming an endoprosthesis, the method comprising:

providing a tubular member having a diameter corresponding to a compressed condition;

forming a plurality of substantially parallelogrammic body cells, wherein each body cell is defined by a pair of parallel long body cell struts intersecting a pair of parallel short body cell struts, the body cells having a body cell elongation ratio of long body cell strut length to short body cell strut length;

forming a plurality of substantially parallelogrammic flare cells, wherein each flare cell is defined by a pair of parallel long flare cell struts intersecting a pair of parallel short flare cell struts, the flare cells having an elongation ratio of long flare cell strut length to short flare cell strut length, and wherein the flare cell elongation ratio is at least approximately 20% greater than said body cell elongation ratio;

forming a plurality of connecting cells, wherein each connecting cell is defined by two pairs of parallel and intersecting connecting cell struts, the struts of the connecting cells have a connecting cell elongation ratio wherein the flare cell elongation ratio is at least approximately 20% greater than the connecting cell elongation ratio, and selected connecting cells are adjacent to at least one body cell and at least one flare cell;

extending at least a substantial portion of each flare cell axially beyond all of the other cells of the endoprosthesis cell structure such that the entire length of one of the short flare cell struts and a substantial portion of each of the pair of long flare cell struts extend axially beyond all of the other cells; and spacing the flare cells apart radially with respect to each other to define free space whereby the first long flare cell strut of one of the flare cells is unconnected to the second long flare cell strut of the adjacent flare cell.

18. The method of claim 17, further including forming the elongation ratio of each flare cell to be approximately 3:1 and forming the elongation ratio of each body cell to be approximately 2:1.

19. The method of claim 17, further including forming each short flare cell strut to have substantially the same length as each short body cell strut.

20. The method of claim 17, further including inclining all of the connecting cell struts, short body cell struts, long body cell struts, short flare cell struts, and long flare cell struts with respect to a longitudinal length of the stent, wherein at least one of the body cells has an upward attitude, at least one of the body cells has a downward attitude, at least one of the flare cells has an upward attitude, and at least one of the flare cells has a downward attitude.

21. The method of claim 20, further including forming in each body cell and each flare cell adjacent to a body cell or flare cell having an opposite attitude.

22. The method of claim 17, further including forming at least one of the connecting cells to have connecting cell struts having substantially the same length as each other.

23. The method of claim 17, further including forming connecting cells other than the selected connecting cells to have connecting cell struts having substantially the same length as each other.

* * * * *